(12) United States Patent
Hall et al.

(10) Patent No.: US 11,549,616 B2
(45) Date of Patent: Jan. 10, 2023

(54) CABLE MANAGEMENT SYSTEM AND CABLE HOLDER

(71) Applicant: Draegerwerk AG & Co. KGaA, Lübeck (DE)

(72) Inventors: Lianna Hall, Phoenix, AZ (US); Ryan Forde, Pelham, NH (US); Juan P. Eslava, Groton, MA (US); Rosaleen Oskanian, Collegeville, PA (US)

(73) Assignee: Draegerwerk AG & Co. KGaA

( * ) Notice: Subject to any disclaimer, the term of this patent is extended or adjusted under 35 U.S.C. 154(b) by 0 days.

(21) Appl. No.: 16/822,893

(22) Filed: Mar. 18, 2020

(65) Prior Publication Data

US 2020/0300385 A1    Sep. 24, 2020

Related U.S. Application Data

(60) Provisional application No. 62/819,797, filed on Mar. 18, 2019.

(51) Int. Cl.
| | |
|---|---|
| *F16L 3/00* | (2006.01) |
| *F16L 3/22* | (2006.01) |
| *F16M 13/02* | (2006.01) |

(52) U.S. Cl.
CPC ............ *F16L 3/222* (2013.01); *F16M 13/02* (2013.01)

(58) Field of Classification Search
CPC ................................. F16M 13/02; F16L 3/222
See application file for complete search history.

(56) References Cited

U.S. PATENT DOCUMENTS

| | | | | |
|---|---|---|---|---|
| 3,696,920 | A * | 10/1972 | Lahay | A61B 50/30 206/370 |
| 4,114,241 | A * | 9/1978 | Bisping | F16L 3/13 248/68.1 |
| 4,852,832 | A * | 8/1989 | Delaney | F16L 3/08 248/65 |
| 5,316,246 | A * | 5/1994 | Scott | A61M 5/1418 248/68.1 |
| 6,109,569 | A * | 8/2000 | Sakaida | F16L 3/222 248/316.7 |
| 8,020,259 | B2 * | 9/2011 | Ho | F16L 3/222 24/129 R |
| 8,074,945 | B2 * | 12/2011 | Schoenau | F16L 5/14 248/65 |
| D657,869 | S * | 4/2012 | Mammen | D24/128 |
| D766,611 | S * | 9/2016 | Bileth | F16M 13/022 D6/512 |
| 10,151,406 | B2 * | 12/2018 | Netke | B60R 16/08 |
| D852,354 | S * | 6/2019 | Wrangmark | F16M 13/022 D24/128 |
| D853,336 | S * | 7/2019 | Barram | A61M 5/1418 D13/155 |

(Continued)

*Primary Examiner* — Amy J. Sterling
(74) *Attorney, Agent, or Firm* — Design IP

(57) ABSTRACT

A cable holder prevents fraying or tangling of cables configured to physically and electrically connect to one or more devices, such as patient monitoring devices. The cable holder can be configured to: (i) detachably secure the one or more cables, and (ii) be detachably secured to a support structure. The cable holder may include a first surface in which an aperture configured to receive a cable is defined, and a second surface on which a connector configured to removably interconnect with a connector of another cable holder is defined.

24 Claims, 10 Drawing Sheets

(56) References Cited

U.S. PATENT DOCUMENTS

| | | | | |
|---|---|---|---|---|
| 10,857,331 | B2 * | 12/2020 | Moudy | A61M 25/02 |
| D907,988 | S * | 1/2021 | Yu | A61B 50/30 |
| | | | | D8/356 |
| D910,572 | S * | 2/2021 | Yang | F16L 3/08 |
| | | | | D13/139.2 |
| 11,095,104 | B2 * | 8/2021 | Frierson | H02G 3/305 |
| D930,459 | S * | 9/2021 | Breines | G06K 19/041 |
| | | | | D8/356 |
| 2005/0189453 | A1 * | 9/2005 | DeGuevara | H02G 3/305 |
| | | | | 248/68.1 |
| 2010/0132979 | A1 * | 6/2010 | Chen | H02G 3/32 |
| | | | | 174/135 |
| 2011/0095089 | A1 * | 4/2011 | Kolton | G06K 19/041 |
| | | | | 235/492 |
| 2011/0248125 | A1 * | 10/2011 | D'Andria | A61M 5/1418 |
| | | | | 248/68.1 |
| 2015/0089774 | A1 * | 4/2015 | Kalejaiye | H02G 3/0437 |
| | | | | 24/122.3 |
| 2016/0114103 | A1 * | 4/2016 | Burke | A61M 5/1415 |
| | | | | 604/179 |
| 2020/0254221 | A1 * | 8/2020 | Burkin | A61M 25/02 |

* cited by examiner

CABLE MANAGEMENT SYSTEM AND CABLE HOLDER

CROSS-REFERENCE TO RELATED APPLICATION(S)

This application claims the benefit of U.S. Provisional Application No. 62/819,797, filed Mar. 18, 2019, which is incorporated herein by reference as if fully set forth.

FIELD OF THE DISCLOSURE AND BACKGROUND

The present disclosure generally relates to a cable management system and a cable holder that can be quickly secured to and released from a support structure and can prevent fraying or tangling of one or more cables configured to physically and electrically connect to one or more devices such as patient monitoring devices.

Conventional cable holders are not adapted to be quickly secured to and released from a support structure and prevent fraying or tangling of cables. Moreover, such conventional cable holders generally cannot reduce cable clutter at the point of care, require complex mounting arrangements, and are not modular. In hospital settings where high acuity care is necessary, cable clutter and complex mounting arrangements are particularly time-consuming and burdensome. Therefore, a need exists to provide a cable holder that can provide at least one or more of the following: quick securement to and release from a support structure, prevention of fraying or tangling of one or more cables, physical and/or electrical connectability to one or more devices such as patient monitoring devices, reduction of cable clutter at the point of care, and/or the ability to be readily cleaned and disinfected.

SUMMARY

The object of the present disclosure is to provide a cable holder that provides flexibility in mounting and cable management by being able to be quickly secured to and released from mobile or transportable support structures such as bed rails, stretcher rails, gurney rails, IV poles, ambulance bars, GCX rails, carts, etc., in addition to stationary support structures such as workstations, ceilings, or walls; and prevent fraying or tangling of one or more cables configured to physically and electrically connect to one or more devices such as patient monitoring devices. The support structure can be, for example, tubular or rectangular. Furthermore, the cable holder of the present disclosure can be modular such that a plurality of the cable holders can be connected in an array so as to manage a plurality of cables.

The cable holder of the present disclosure can be standardized and can consolidate a plurality of cables such as shielded cables and ribbon cables. The cable holder of the present disclosure can protect the cables from potential sources of contamination. The cable holder of the present disclosure therefore optimizes the workplace by reducing cleaning and disinfection time, improving workplace organization, reducing the risk of equipment being accidentally disconnected, optimizing workflow through well-structured workplace design, and reducing the risk of contamination. In other words, the cable holder of the present disclosure can keep lines and cables out of the way and free of dust and other potential contaminants so as to help maintain a clutter-free workspace and prevent microbial contamination of equipment and patients. For example, nosocomial infections are a significant source of morbidity and mortality.

Tangled cables can cause a great deal of frustration, lost time, and patient discomfort. Managing the clutter that results from conventional cables is a tedious, time-consuming distraction that takes focus away from patient care. As cables are attached, they must be untangled and properly routed. The cable holder of the present disclosure enables caregivers to spend more time with patients and less time sorting out cables. The cable holder of the present disclosure eliminates the tangled clutter and hazards, in the operation room and intensive care unit, for example, that frequently occur with traditional cables and reduces visual overload for patients. The cable holder of the present disclosure is flexible, durable, fast and easy to apply to a support structure, and is easy to clean because it wipes clean with standard disinfectants.

A system of the present disclosure may include a support structure, a cable holder and a cable. The cable can be configured to be detachably secured to the cable holder. The cable holder can be configured to be detachably secured to the support structure. The cable holder of the present disclosure can be configured to detachably secure the one or more cables, and can be configured to be detachably secured to a support structure. The cable holder of the present disclosure may include a first surface in which an aperture configured to receive a cable is defined. The cable holder of the present disclosure may include a second surface on which a connector configured to mate with a connector of another cable holder is defined. The connector can be a mechanically interlockable connector. The connector may include a male protrusion and/or a female recess. The connector may include a connector array of magnets having a specific connector magnetic polarity pattern. The first surface and the second surface can be on adjacent or opposite sides of the cable holder of the present disclosure.

DETAILED DESCRIPTION

Figure 1:
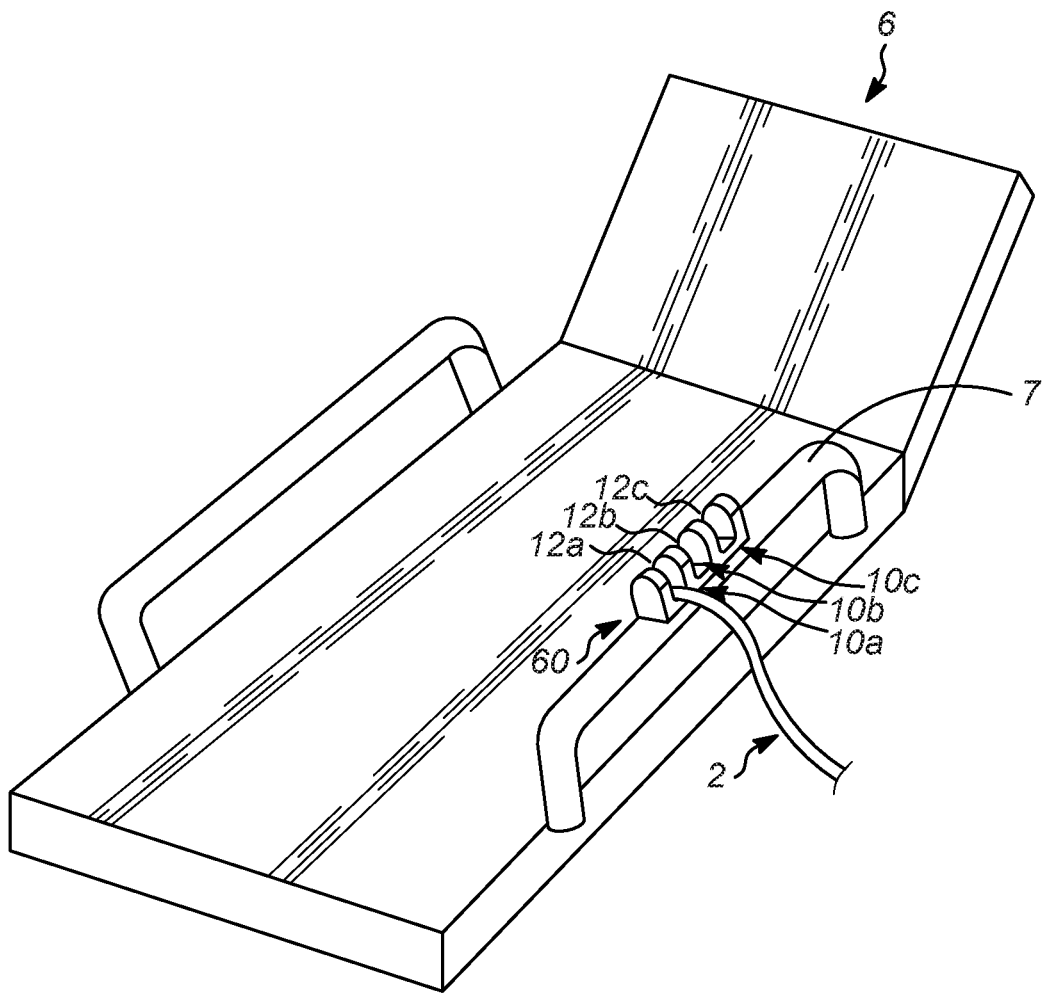
FIG. 1 is a perspective view illustrating an example system including a first exemplary implementation of cable holders, a cable, and a support structure.

The following description is made with reference to the accompanying drawings and is provided to assist in a comprehensive understanding of various example embodiments of the present disclosure. The following description includes various details to assist in that understanding, but these are to be regarded as merely examples. Accordingly, those of ordinary skill in the art will recognize that various changes and modifications of the examples described herein can be made without departing from the spirit and scope of the present disclosure. In addition, descriptions of well-known functions and constructions may be omitted for clarity and conciseness.

The terms and words used in the following description and claims are not limited to the bibliographical meanings, but are merely used to enable a clear and consistent understanding of the present disclosure. Accordingly, it should be apparent to those skilled in the art that the following description of the present disclosure is provided for illustration purposes only, and not for the purpose of limiting the present disclosure as defined by the appended claims and their equivalents.

It is to be understood that the singular forms "a", "an", and "the", include plural referents unless the context clearly dictates otherwise. Thus, for example, reference to "a cable holder" or "a cable" includes reference to one or more of such cable holders or cables.

The expressions such as "include" and "may include" which may be used in the present disclosure denote the presence of the disclosed functions, operations, and constituent elements, and do not limit the presence of one or more additional functions, operations, and constituent elements. In the present disclosure, terms such as "include" and/or "have", may be construed to denote a certain characteristic, number, operation, constituent element, component or a combination thereof, but should not be construed to exclude the existence of or a possibility of the addition of one or more other characteristics, numbers, operations, constituent elements, components or combinations thereof.

In the present disclosure, the expression "and/or" includes any and all combinations of the associated listed words. For example, the expression "A and/or B" may include A, may include B, or may include both A and B.

In the present disclosure, expressions including ordinal numbers, such as "first", "second", and/or the like, may modify various elements. However, such elements are not limited by the above expressions nor do the above expressions imply that there are just the requisite number of elements present. For example, the above expressions do not limit the sequence and/or importance of the elements. The above expressions are used merely for the purpose of distinguishing an element from the other elements. For example, a first box and a second box indicate different boxes, although both are boxes. For further example, a first element could be termed a second element, and similarly, a second element could also be termed a first element without departing from the scope of the present disclosure.

As used herein, the term "removably interconnect" or "removably interconnected" is intended to mean that the elements in question are adapted to be connected in a manner the prevents them from separating from one another without the application of a substantial separating force and that the elements can be separated without damaging either element. Examples of structures that are adapted to be removably interconnected include complimentary-shaped protrusions and recesses that provide a friction fit (such as those shown in FIG. 5) and magnetic elements with polarity orientations and/or patterns that cause the elements to be attracted to one another. The term "mechanical interlock" is a subset of the types of connections that are "removably interconnectable."

As used herein, the term "line of weakness" is intended to mean a line that traverses the width of the element in question along with the tearing resistance of that element is weakened, so as to facilitate separation of the element into two portions along the line of weakness. Examples of methods of creating lines of weakness include, but are not limited to, perforating, skip-cutting, scoring, nicking, and laser ablation.

Unless otherwise defined, all terms including technical and/or scientific terms used herein have the same meaning as commonly understood by one of ordinary skill in the art to which the present disclosure pertains. In addition, unless otherwise defined, all terms defined in generally used dictionaries may not be overly interpreted.

The subject matter described herein is directed to a cable management system and a cable holder directed to devices such as a patient monitor, a physiological sensor and/or medical device, and a module. A patient monitor is used by healthcare facilities to monitor and display information about a patient, such as vital signs, status of connected devices (e.g., physiological sensors, etc.), and the like. A patient monitor can be a portable device that travels with the patient in order to provide continuous monitoring during care. A physiological sensor and/or medical device can be, for example, an ECG electrode, a $S_pO2$ sensor, a blood pressure cuff, an apnea detection sensor, a respirator, etc., and can monitor a physiological parameter of a patient (e.g., gas measurement, end-tidal carbon dioxide (etCO2), SCIO, patient gas, thermoregulation, blood pressure, heart related measurement, pulse oximetry, respiration, neonatal measurement, ventilation, anesthesia information, incubation information, etc.). A module can provide one or more different functions used in delivering healthcare to a patient. A module can acquire patient data including the monitored parameters allocated to a given patient from a network and collate the information for storage in a database. A module can be any of a patient monitoring module for acquiring and processing data generated by at least one physiological sensor, a patient treatment module for delivering treatment to the patient (e.g., monitoring fluids administered to the patient and supplying anesthesia to the patient, respectively), a control module, a charging module, a compartment module, a converter module, a transmitter module, a relay module, a battery module, a camera module, a purge module, a robot module, an internal and/or external communication module, a power supply module, a global positioning system (GPS) module, a mobile and/or stationary data transfer module, an output board, a facility module, a Trace Work Area (TWA) control module, an output board, a dock module, an adapter module, a passive treatment module, an active treatment module, etc. Use of such systems and apparatuses can, for example, occur in a medical environment such as the scene of a medical event, an ambulance, a hospital or a doctor's office.

FIG. 1 is a perspective view illustrating an example system including a first exemplary implementation of cable holders 10a, 10b, 10c, a cable 2, and a support structure 6.

In the embodiment shown in FIG. 1, each of the cable holders 10a-10c includes an aperture (see apertures 12a-12c). The aperture 12a, 12b, 12c may be a channel configured to receive a side of the cable 2 such that the cable 2 is seated in the channel and is detachably secured to the corresponding cable holder 10a, 10b, 10c. In certain embodiments, the channel may be U-shaped (such as the embodiment shown in FIG. 1) or C-shaped. As shown in the embodiment of FIG. 1, the cable holders 10a-10c may be arranged in an integrated or single-piece construction array 60. Each of the cable holders 10a-10c can detachably secure a cable 2 therein. The cable holders 10a-10c may be mounted to a rail 7 of the support structure 6. The support structure 6 may be, for example, a bed. Alternatively, as shown in the embodiment of FIG. 3 or the embodiment of FIG. 5, for example, the cable holder 10 may be one of a plurality of separate and discrete cable holders removably interconnected to each other whereby each of the cable holders detachably secures a cable 2 therein.

Figure 2:
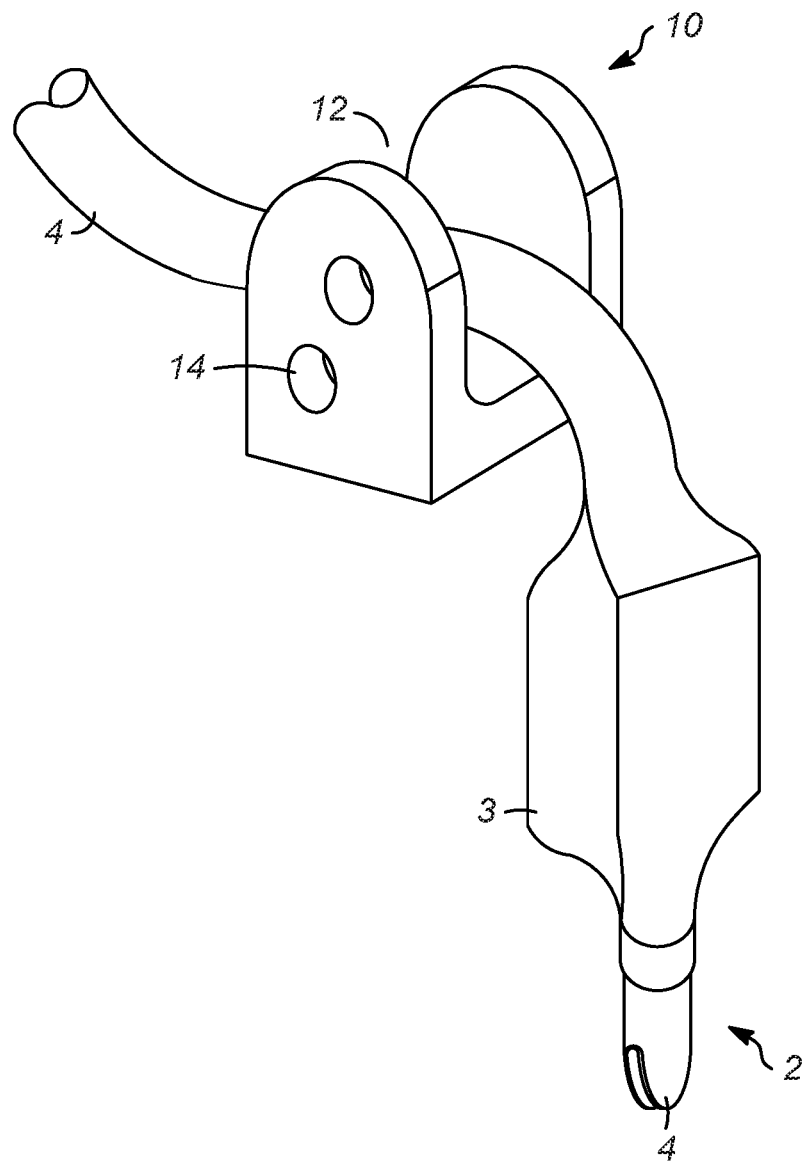
FIG. 2 is a perspective view illustrating the example system including the first exemplary implementation of the cable holder, and a cable.

FIG. 2 is a perspective view illustrating the example system including the first exemplary implementation of the cable holder 10, and a cable 2. The cable holder 10 may include a connector 14 for connecting to another cable holder. The connector 14 may comprise a female connector or recess. The connector 14 may alternatively or additionally comprise a male connector or protrusion. The cable 2 may include a housing portion 3 and cable portions 4. The cable holder 10 may be configured to directly hold the cable portions 4. The housing portion 3 may be configured to house, for example, one or more circuit, processor, or memory boards (not shown) configured to perform one or more functions such as, for example, translating protocols across the cable portions 4. The housing portion 3 may be located medially in the cable 2 between the cable portions 4. The housing portion 3 may be wider than the cable portions 4. In some variations, the cable holder 10 may further include a retaining portion (not shown) in the channel for retaining the cable 2. The cable 2 may be detachably secured in the cable holder 10 such that the cable 2 is under tension.

Figure 3:
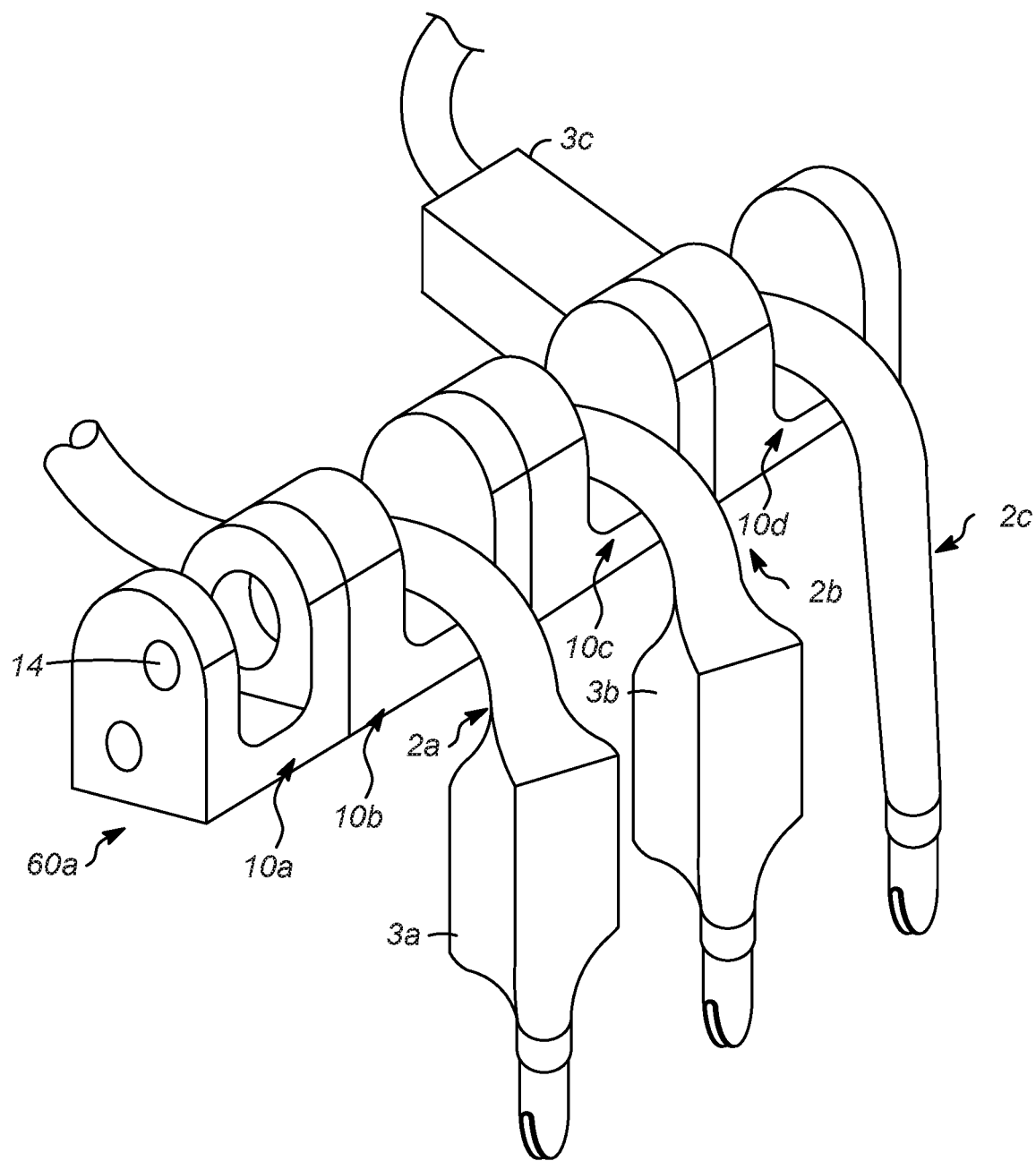
FIG. 3 is a perspective view illustrating the example system including the first exemplary implementation of the cable holders, and cables.

FIG. 3 is a perspective view illustrating the example system including the first exemplary implementation of cable holders 10a-10d, and cables 2a-2c. As shown in the embodiment of FIG. 3, the cable holders 10a-10d may be separate and discrete and arranged in an array 60a such that each of the cable holders 10a-10d detachably secures a cable 2 therein. The array 60a may comprise two or more of the cable holders 10a-10d arranged such that at least two connectors (not shown) of the cable holders 10a-10d are mechanically interlocked. In implementations not shown, each of the cables 2a-2c may have a different length such that the housing portions 3a-3c are staggered.

Figure 4:
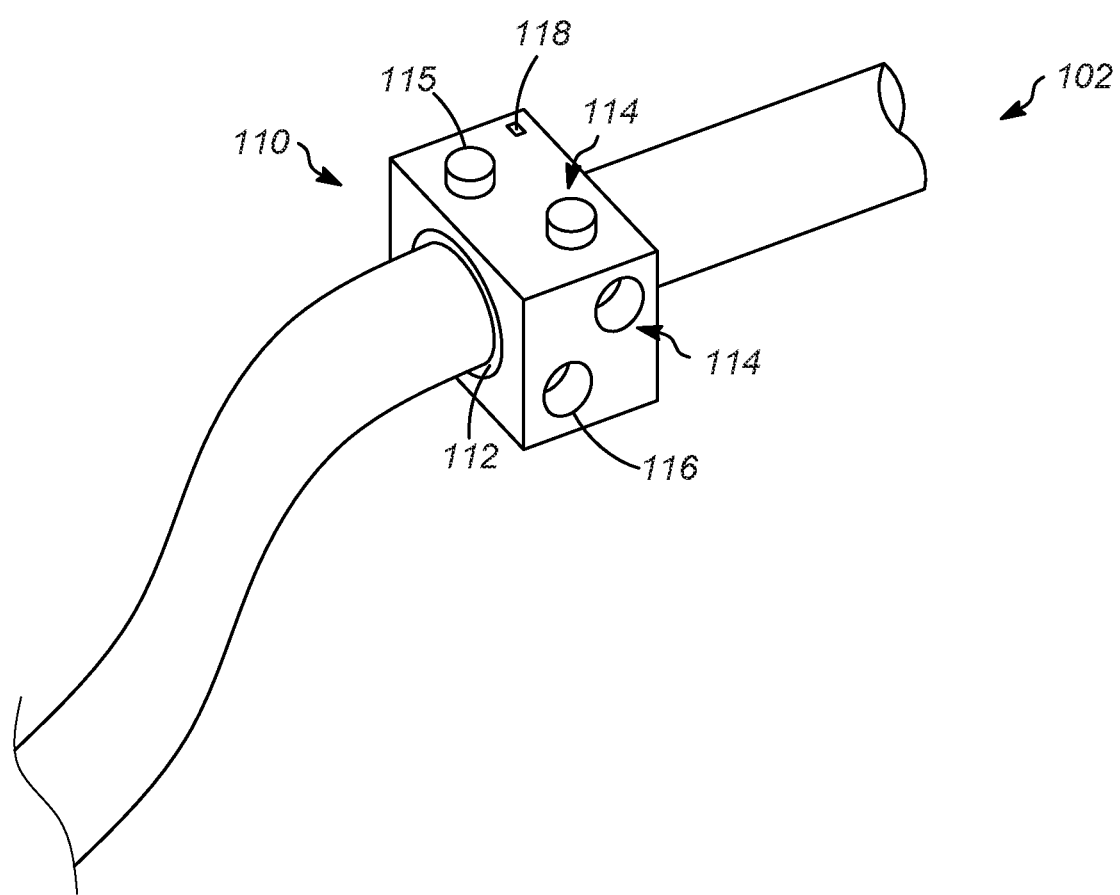
FIG. 4 is a perspective view illustrating the example system including a second exemplary implementation of the cable holder, and a cable.

FIG. 4 is a perspective view illustrating a second example system including a second exemplary implementation of a cable holder 110 and a cable 102. In the second exemplary embodiment, elements shared with the first embodiment are represented by reference numerals increased by 100. For example, the cable 102 of the first exemplary embodiment corresponds to the cable 102 of the second exemplary embodiment. In the interest of brevity, the reference numerals of some features of this embodiment that are shared and described in connection with the first embodiment appear in the figures but are not provided in the specification. The foregoing applies in the same manner to each subsequent embodiment, except that the reference numerals used in each embodiment increase by 200, 300, 400, or 500, respectively.

The cable holder 110 may include at least one connector 114. A connector 114 of the cable holder 110 may be a mechanically interlockable connector configured to mechanically interlock with a connector of another cable holder (not shown). A connector 114 may include a male connector 115 and/or a female connector 116. The cable holder 110 may include two apertures (see first aperture 112; second aperture not shown) on opposite or adjacent sides of the cable holder 10 whereby the cable 102 extends through both apertures. In other words, the apertures may define a through-hole extending all the way through the cable holder 110. The embodiment shown in FIG. 4 further comprises a radio frequency identification (RFID) tag 118 for analytics, key performance indicators, identification and/or tracking purposes so that usage, location and functionality of the cable holder 110 can be observed throughout a hospital, for example.

Figure 5:
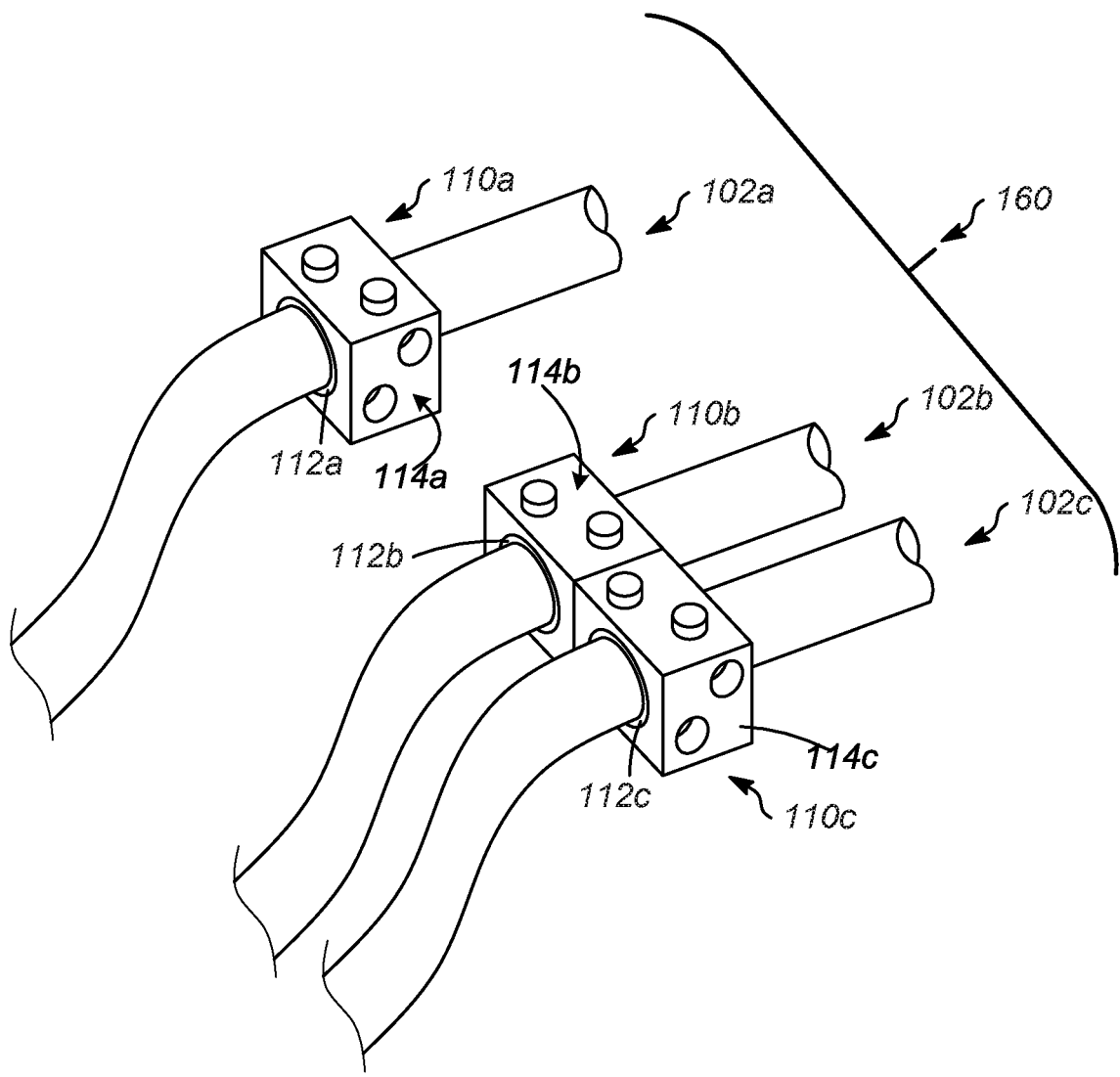
FIG. 5 is a perspective view illustrating the example system including the second exemplary implementation of the cable holders, and cables.

FIG. 5 is a perspective view illustrating the second example system including the second exemplary implementation of cable holders 110a, 110b, 110c, and cables 102a, 102b, 102c. As shown in the embodiment of FIG. 5, the cable holders 110a-110c may be separate and discrete and arranged in an array 160 whereby each of the cable holders 110a-110c detachably secures a corresponding one of the cables 102a-102c therein. The array 160 may comprise two or more of the cable holders 110a-110c arranged such that at least two of the connectors 114a-114c of a corresponding two or more of the cable holders 110a-110c are mechanically interlocked. In this embodiment, the cable holders 110a-110c are arranged in a horizontal linear array, meaning that the array 160 of cable holders 110a-110c are arranged side-by-side and along a single axis.

Figure 6:
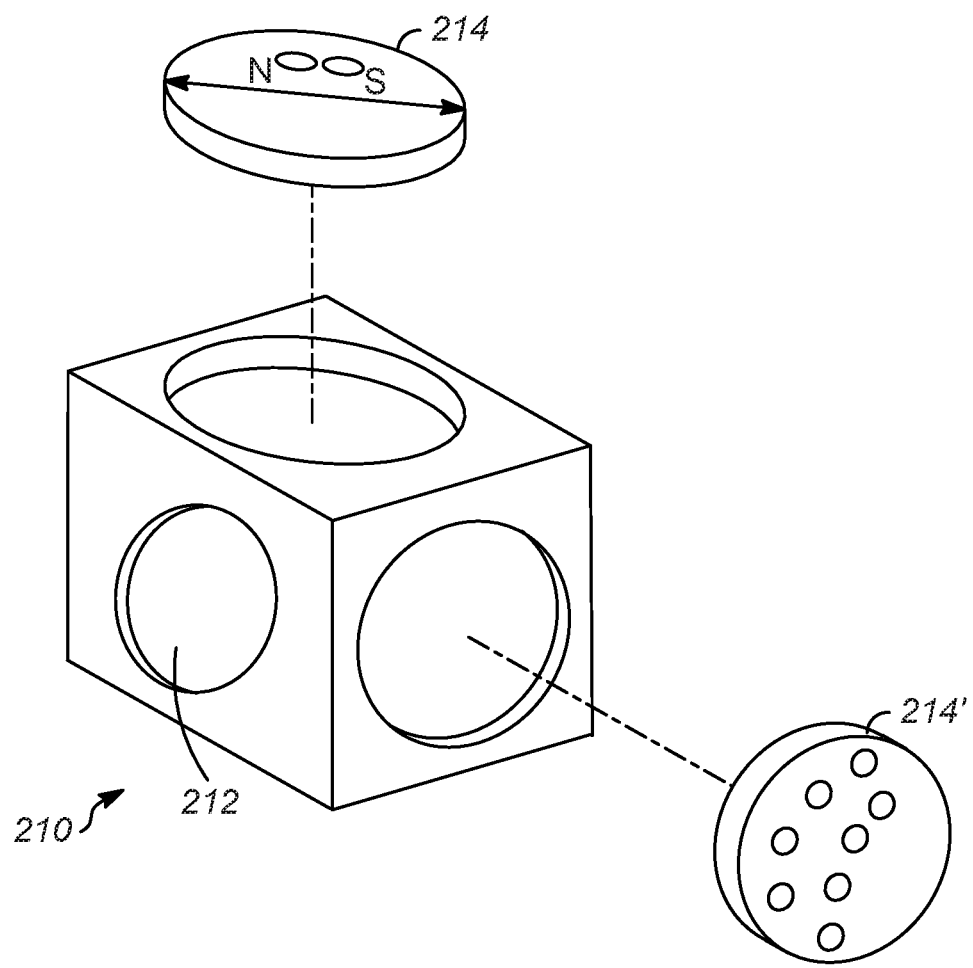
FIG. 6 is a perspective view of a third exemplary implementation of the cable holder.

FIG. 6 is a perspective view of a third exemplary implementation of a cable holder 210. The cable holder 210 may include at least one connector 214. The connector 214 of the cable holder 210 may be a magnetic connector configured to be attracted to a connector of another cable holder (not shown). The connector 214 may include an array of magnets having a magnetic polarity pattern that is complementary to a magnetic polarity pattern of the connector of the other cable holder. In one example, the array of magnets of the connector 214 might comprise different regions (magnet pixels, called maxels) of a single piece of magnetizable material, to form a multi-pole correlated magnetic structure in which the regions differ from each other in terms of magnetic polarity and/or magnetic strength (compare connector 214 with connector 214'). In another example, some or all of the array of magnets might be electromagnets such as electrically activated coils that are activated (controlled) by a controller (not shown). The array of magnets of the connector 214 might be narrower than 2 mm, and might be spaced apart by less than 3 mm. Accordingly, the magnetics of the connectors 214, 214' can be used to organize cables in desired orientations.

Figure 7:
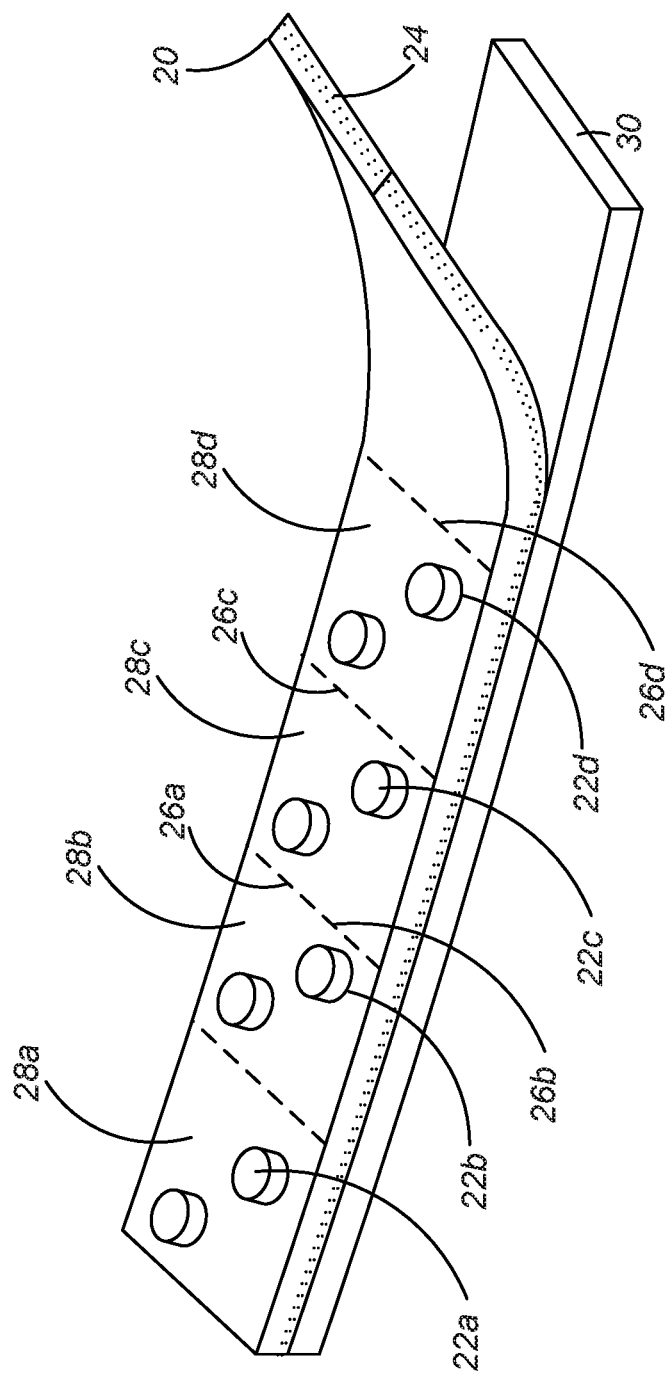
FIG. 7 is a perspective view of an attachment structure including a mounting portion and a removable backing.

FIG. 7 is a perspective view of an attachment structure including a mounting portion 20 (also referred to herein as a mounting strip) and a removable backing 30. The mounting portion 20 may include one or more connectors 22a-22d configured to mate with the connectors (e.g., connector 14) of the cable holder (e.g., cable holder 10) of any of the embodiments described herein. The mounting portion 20 may include an adhesive portion 24 configured to be bonded to the support structure 6 (see FIG. 1). The adhesive portion 24 may be adapted to be bonded to any of multiple different types of surfaces. In this way, the mounting portion 20 can first be affixed to a support structure 6 via the adhesive portion 24, and then to the connecter 14 of the cable holder 10 can be connected to one of the connectors 22a-22d of the mounting portion 20. Alternatively, the connector 14 of the cable holder 10 can first be connected to one of the connectors 22a-22d of the mounting portion 20, and then the mounting portion 20 can be affixed to the support structure 6 via the adhesive portion 24. The removable backing 30 may be configured to cover the adhesive portion 24 prior to use. The mounting portion 20 may further include lines of weakness 26a-26d defined in a surface of the mounting portion 20. Each of the lines of weakness 26a-26d may be adjacent to a corresponding one of the connectors 22a-22d. The lines of weakness 26a-26d may divide the mounting portion 20 into segments 28a-28d. Accordingly, the lines of weakness 26a-26d enable customization of the length of the mounting portion 20 through selection of a desired number of segments 28a-28d for mounting to a support structure 6. For example, any desired number of segments 28a-26d can be torn away, broken off, or otherwise detached from the mounting portion 20. In one embodiment, a line of weakness 26a-26d is provided between each of the connectors 22a-22d. In another embodiment, the lines of weakness are only provided between groups of connectors (e.g., only including lines of weakness 26b and 26d).

Figure 8A:
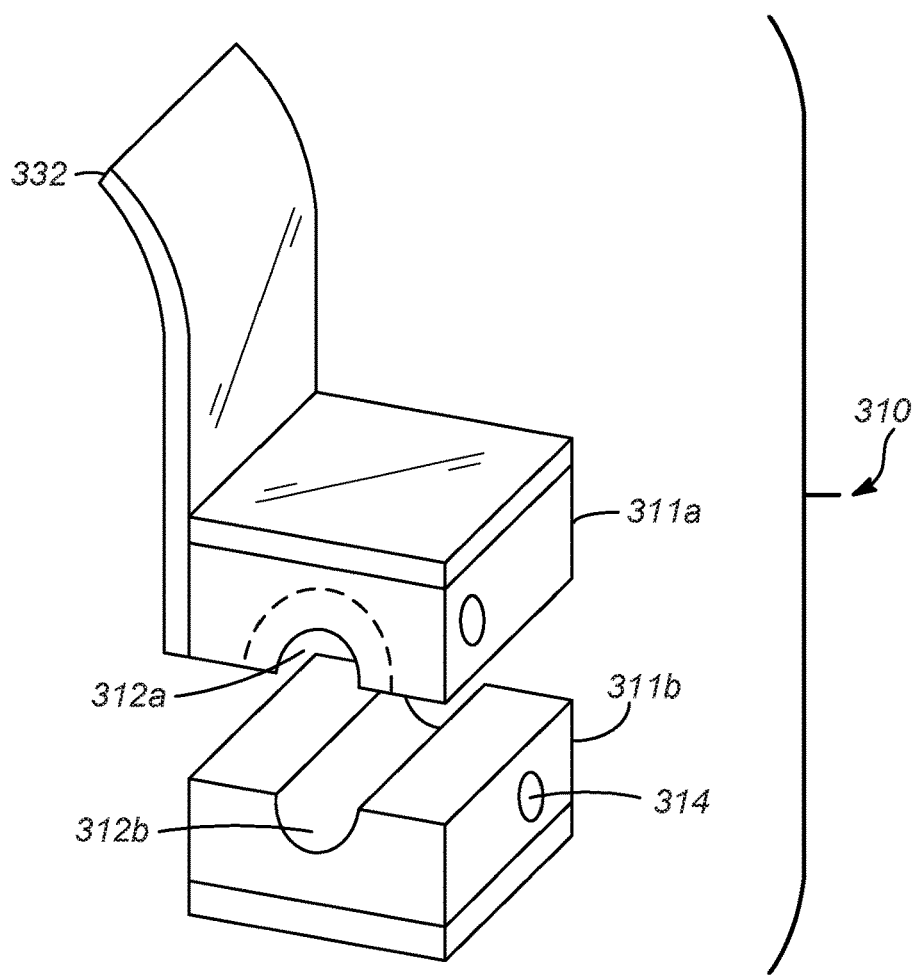
FIG. 8A is a perspective view of a fourth exemplary implementation of the cable holder.
Figure 8B:
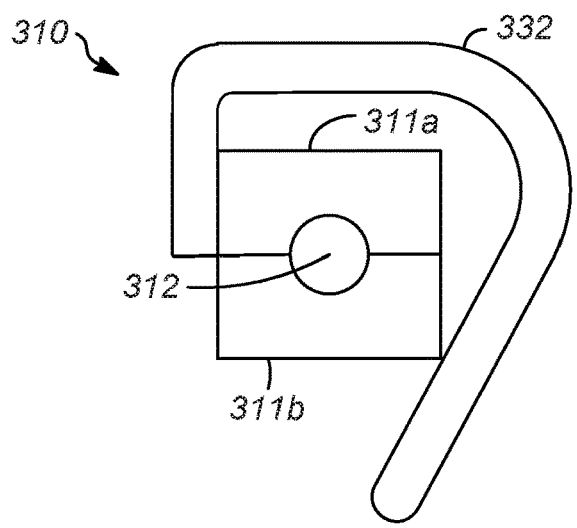
FIG. 8B is a side view of the fourth exemplary implementation of the cable holder.
Figure 8C:
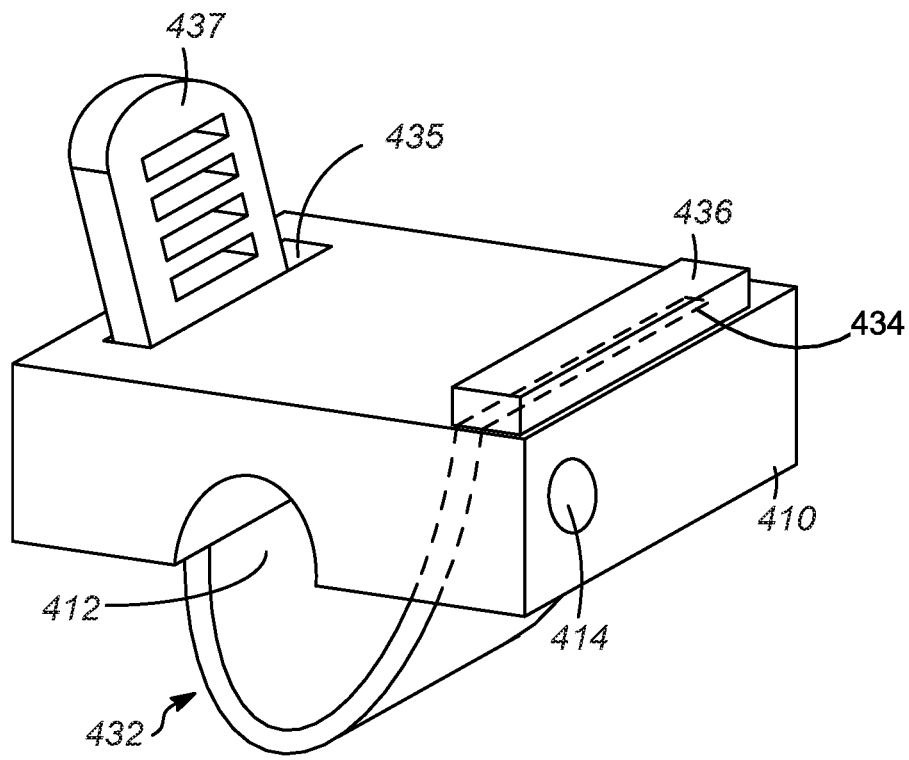
FIG. 8C is a perspective view of a fifth exemplary implementation of the cable holder.

FIGS. 8A-8C are views of a fourth exemplary implementation of the cable holder 310. The cable holder 310 may be formed from first and second interfitting pieces 311b, 311b, which are separable. The first and second interfitting pieces 311a, 311b may be U-shaped or C-shaped. A first portion 312a of the aperture 312 may be defined in the first interfitting piece 311a and a second part 312b of the aperture 312 may be defined in the second interfitting piece 311b. The cable holder 310 may further comprise a strap or an adjustable band 332 extending from one of the first and second interfitting pieces 311a, 311b and being configured to hold the combined first and second interfitting pieces 311a, 311b together.

In the fifth exemplary embodiment shown in FIG. 8C, the cable holder 410 may further comprise a first recess 434 and a second recess 435 whereby the adjustable band 432 is insertable through the first recess 434 and the second recess 435 such that a first end 436 of the adjustable band 432 is fixed in the first recess 434 and a second end 437 of the adjustable band 432 extends through the second recess 437 such that the adjustable band 432 is configured to adjustably and detachably secure a cable to the cable holder 410, using a structure similar to a conventional cable tie.

Figure 9A:
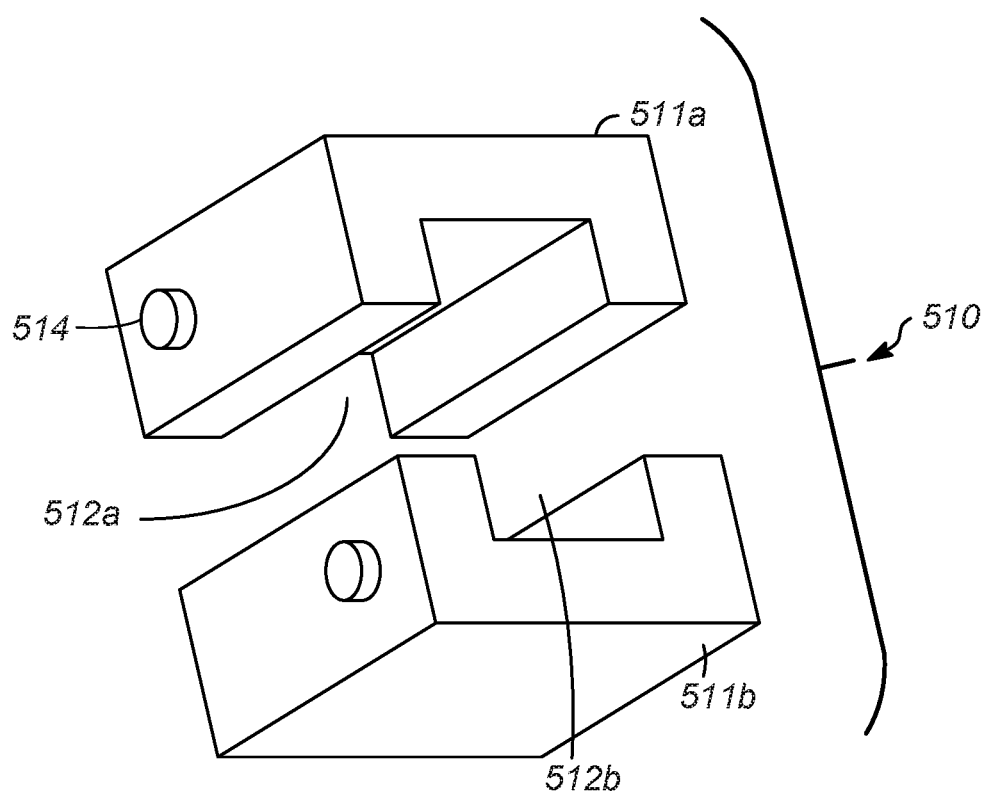
FIG. 9A is a side view of a sixth exemplary implementation of the cable holder.
Figure 9B:
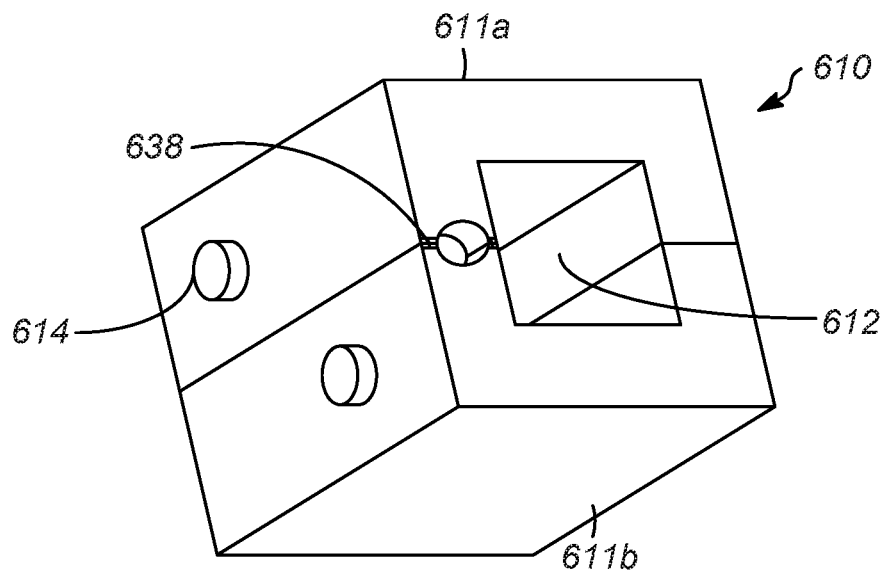
FIG. 9B is a side view of the seventh exemplary implementation of the cable holder.
Figure 9C:
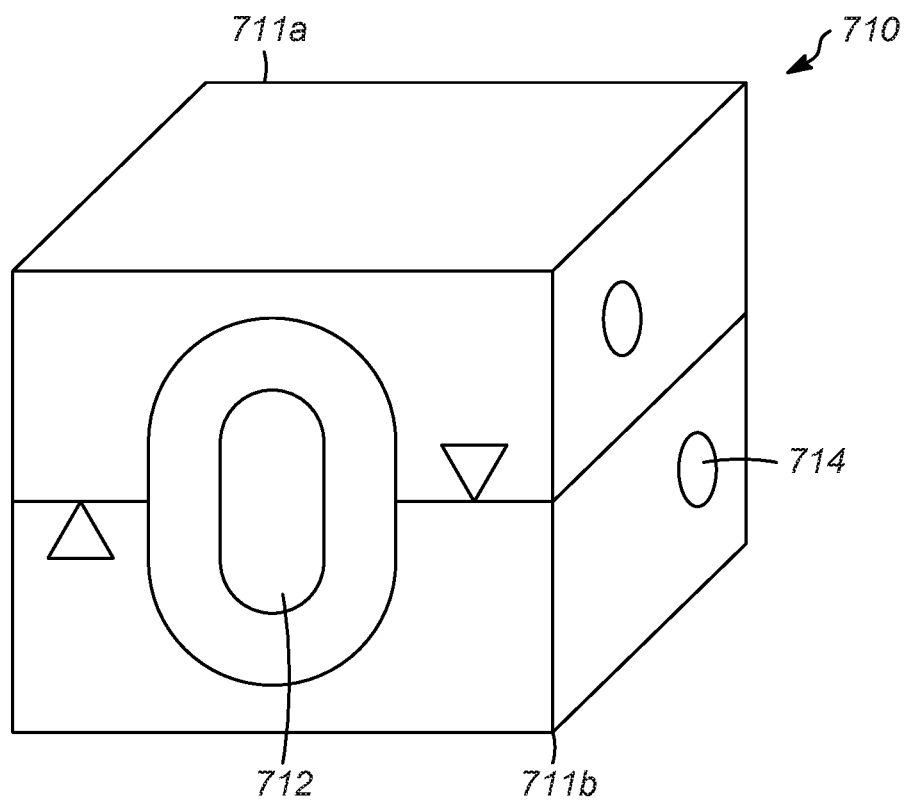
FIG. 9C is a perspective view of an eighth exemplary implementation of the cable holder.

FIGS. 9A-9C are views of additional exemplary implementations of a cable holder 510, 610, 710. The cable holders 510, 510, 710 may each be formed from two interfitting pieces (first and second interfitting pieces 511a, 511b in FIG. 9A; first and second interfitting pieces 611a, 611b in FIG. 9B; first and second interfitting pieces 711a, 711b in FIG. 9C) which are separable. The interfitting pieces of the cable holders 510, 610, 710 may be shaped in a manner to accommodate a cable. For example, the first and second interfitting pieces 511a, 511b of the cable holder 510 shown in FIG. 9A are C-shaped, creating a square cross-section for the aperture 512, while the first and second interfitting pieces 711a, 711b of the cable holder 710 are U-shaped, creating an oblong cross-section for the aperture 712 shown in FIG. 9C. As seen in FIG. 9A, a first part 512a of the aperture 512 may be defined in the first interfitting piece 511a and a second part 512b of the aperture 512 may be defined in the second interfitting piece 511b. In the embodiment shown in FIG. 9B, the cable holder 610 includes a hinge 638 that connects the first and second interfitting pieces 611a, 611b.

In some embodiments (not shown), the interfitting pieces of a cable holder may include respective magnets having opposite polarities such that the magnets are attracted to each other. In other variations (not shown), the interfitting pieces of a cable holder may include respective mechanically interlocking connectors configured to mechanically interlock with each other.

In any of the embodiments, any number of connectors 14 could be located on any surface of the cable holders 10. Any of the cable holders 10 may be comprised of plastic. Therefore, the cable holders 10 provide flexibility in manufacturing, mounting and cable management. Cables 2 can be easily secured by the cable holders 10 rather than dangling and causing inconvenience on transport or at a stationary setting. Such a cable management solution frees up space and is helpful with respect to seamless workflow in a variety of areas such as monitoring, anesthesia, and information technology workstations. The system of the present disclosure provides a universal and scalable platform including a cable holder capable of being quickly secured to and released from a support structure and preventing fraying or tangling of one or more cables configured to physically and electrically connect to one or more devices such as patient monitoring devices.

For example, any feature of any particular portion, embodiment or modification of the cable holder 10 may be included or omitted from any of the other portions, embodiments or modifications of the cable holder 10. As a particular example, the RFID tag 118 shown in the embodiment shown in FIG. 4 may be included in any of the cable holders 10, 110, 210, 310, 410, 510.

It is also contemplated that the implementation of the components of the present disclosure can be done with any newly arising technology that may replace any of the above implementation technologies.

Although various embodiments have been described above, these are to be regarded as merely examples. Accordingly, those of ordinary skill in the art will recognize that various changes and modifications of the examples described herein can be made without departing from the spirit and scope of the present disclosure.

What is claimed is:
1. An apparatus comprising:
a plurality of cable holders, each of the plurality of cable holders comprising
a cable-receiving aperture operationally configured to removably secure a cable therein; and
a first cable holder connector; and
a plurality of second cable holder connectors, each of the second cable holder connectors being complimentary in shape to the first cable holder connector of each of the plurality of cable holders;
wherein each of the plurality of second cable holder connectors being formed in at least one selected from the group of: (a) one of the plurality of cable holders and (b) a mounting strip;
wherein the first cable holder connector of each of the plurality of cable holders is adapted to removably interconnect with any of the plurality of second cable holder connectors; and,
wherein the cable-receiving aperture includes a lower surface located at a lowermost edge of the cable-receiving aperture, and the first cable holder connector comprises a plurality of first cable holder connectors, and at least a portion of the plurality of first cable holder connectors is positioned above the lower surface of the cable-receiving aperture.

2. The apparatus of claim 1, wherein each of the plurality of second cable holder connectors is formed in one of the plurality of cable holders.

3. The apparatus of claim 1, wherein a first set of the plurality of second cable holder connectors is formed in the plurality of cable holders and a second set of the plurality of second cable holder connectors is formed in the mounting strip.

4. The apparatus of claim 1, wherein a first set of the plurality of second cable holder connectors is formed in the mounting strip.

5. The apparatus of claim 4, wherein the mounting strip comprises an adhesive backing.

6. The apparatus of claim 4, wherein the mounting strip comprises a plurality of segments, each of the plurality of segments being separated by a line of weakness, wherein at least one of the first set of the plurality of second cable holder connectors is located in each of the plurality of segments.

7. The apparatus of claim 1, wherein the first cable holder connector of each of the plurality of cable holders is complimentary in shape to each of the plurality of second cable holder connectors.

8. The apparatus of claim 1, wherein the first cable holder connector of each of the plurality of cable holders comprises a first pattern having at least one selected from the group of a male protrusion and a female recess and each of the plurality of second cable holder connectors comprises a second pattern having at least one selected from the group of a male protrusion and a female recess, the first pattern and the second pattern being complimentary in shape.

9. The apparatus of claim 1, wherein the first cable holder connector of each of the plurality of cable holders comprises a first array of magnets having a first polarity pattern and each of the plurality of cable holder connectors comprises a second array of magnets having a second polarity pattern, the first polarity pattern being complimentary to the second polarity pattern.

10. The apparatus of claim 1, wherein each of the plurality of cable holders further comprises a first portion and a second portion, wherein the first and second portions are adapted to be removably interconnected, wherein the cable-receiving aperture is adapted to encircle the cable when the first and second portions are interconnected.

11. The apparatus of claim 10, wherein each of the plurality of cable holders further comprises a hinge that pivotably connects the first portion to the second portion.

12. The apparatus of claim 1, wherein each of the plurality of cable holders further comprises two recesses formed and an adjustable band that extends through the two recesses, wherein the cable-receiving aperture is defined by the adjustable band.

13. The apparatus of claim 1, wherein each of the plurality of cable holders comprises an RFID tag.

14. The apparatus of claim 1, wherein the first cable holder connector and the plurality of second cable holder connectors are located on side walls of the plurality of cable holders and arranged to interconnect the plurality of cable holders in abutting relationships.

15. The apparatus of claim 1, wherein the first cable holder connector and the plurality of second cable holder connectors are arranged to interconnect the plurality of cable holders and prevent rotational movement between the plurality of cable holders when interconnected.

16. The apparatus of claim 1, wherein each of the plurality of second cable holder connectors is formed in a mounting strip.

17. The apparatus of claim 1, wherein each of the plurality of second cable holder connectors is in the form of a cylindrical protrusion.

18. The apparatus of claim 1, wherein the cable-receiving aperture comprises a channel including side walls that extend upwardly from a lower surface in a non-narrowing fashion.

19. The apparatus of claim 18, wherein the side walls of the cable-receiving aperture are substantially planar and parallel to each other.

20. The apparatus of claim 18, wherein the lower surface of the cable-receiving aperture includes a flattened portion.

21. The apparatus of claim 18, wherein the side walls of the cable-receiving aperture are adapted to accept a cable without deforming during receipt of the cable therein.

22. The apparatus of claim 1, wherein the cable-receiving aperture is a U-shaped channel.

23. The apparatus of claim 1, wherein each of the plurality of first cable holder connectors is in the form of a cylindrical protrusion, and wherein each of the plurality of second cable holder connectors is in the form of a cylindrical recess that is shaped and arranged to interconnect with one of the plurality of first cable holder connectors.

24. The apparatus of claim 18, wherein each of the plurality of second cable holder connectors is in the form of a cylindrical recess that extends through one of the side walls, thereby being exposed to the channel.

* * * * *